(12) United States Patent
Damit (10) Patent No.: US 9,943,845 B2
(45) Date of Patent: Apr. 17, 2018

(54) DETECTOR AND METHOD FOR DETECTING AN AGENT IN AN AEROSOL

(71) Applicant: The Johns Hopkins University, Baltimore, MD (US)

(72) Inventor: Brian E. Damit, Silver Spring, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/338,024

(22) Filed: Oct. 28, 2016

(65) Prior Publication Data

US 2017/0122870 A1    May 4, 2017

Related U.S. Application Data

(60) Provisional application No. 62/247,304, filed on Oct. 28, 2015.

(51) Int. Cl.
| | |
|---|---|
| *B01L 3/00* | (2006.01) |
| *G01N 21/64* | (2006.01) |
| *G01N 1/22* | (2006.01) |
| *G01N 21/77* | (2006.01) |
| *G01N 15/00* | (2006.01) |

(52) U.S. Cl.
CPC .......... *B01L 3/5027* (2013.01); *G01N 1/2208* (2013.01); *G01N 21/6458* (2013.01); *G01N 2001/2223* (2013.01); *G01N 2015/0046* (2013.01); *G01N 2021/7786* (2013.01)

(58) Field of Classification Search
CPC ............................... G01N 1/00; B01L 3/5027
USPC .......................................................... 356/36
See application file for complete search history.

(56) References Cited

U.S. PATENT DOCUMENTS 5,906,670 A * 5/1999 Dobson ..................... B22F 9/26
257/17

* cited by examiner

*Primary Examiner* — Roy M Punnoose
(74) *Attorney, Agent, or Firm* — Todd R. Farnsworth (57) ABSTRACT

A detector for detecting an agent within an aerosol is provided. The detector may include a liquid feeder configured to generate a droplet comprised of an assay reagent. The detector may further include an aerosol focuser configured to capture and focus the aerosol such that the aerosol is configured to be encapsulated within the droplet in order to cause the assay reagent to react in the droplet. The detector may even further include an interrogator configured to interrogate the droplet in order to detect the agent within the aerosol.

20 Claims, 11 Drawing Sheets

FIG. 1

```
         ┌─────────────────────┐
         │   AEROSOL FOCUSER   │— 140
         └─────────────────────┘
                    │
                    ▼
         ┌─────────────────────┐
    120—│    LIQUID           │
         │    FEEDER           │
         └─────────────────────┘
                    ▲
                    │
         ┌─────────────────────┐
         │    INTERROGATOR     │— 160
         └─────────────────────┘
```

FIG. 11

DETECTOR AND METHOD FOR DETECTING AN AGENT IN AN AEROSOL

CROSS-REFERENCE TO RELATED APPLICATIONS

This application claims priority to and the benefit of prior-filed U.S. Provisional Application Ser. No. 62/247,304, filed Oct. 28, 2015, the content of which is herein incorporated by reference in its entirety.

TECHNICAL FIELD

Example embodiments relate generally to detectors and methods for detecting agents in an aerosol, and more particularly to detectors and methods that utilize microfluidics to detect agents in an aerosol.

BACKGROUND

Rapid identification of agents is crucial in the event of terrorist attacks or disease outbreaks. Current identification methods, however, require transporting samples to laboratories and may take upwards of several days to detect and identify the agents. Accordingly, precautionary measures such as shutting down entire cities and quarantining large amounts of people may be required if an agent is suspected. Moreover, current agent detection methods typically have low sensitivity and require expensive consumption of reagents.

BRIEF SUMMARY OF SOME EXAMPLES

An example embodiment may provide a detector for detecting an agent within an aerosol. The detector may include a liquid feeder configured to generate a droplet comprised of an assay reagent. The detector may further include an aerosol focuser configured to capture and focus the aerosol such that the aerosol is configured to be encapsulated within the droplet in order to cause the assay reagent to react in the droplet. The detector may even further include an interrogator configured to interrogate the droplet in order to detect the agent within the aerosol.

In an example embodiment, a method for detecting an agent within an aerosol may be provided. The method may include generating a droplet including an assay reagent via a liquid feeder. The method may also include capturing and focusing the aerosol via an aerosol focuser, and interrogating the droplet with an interrogator in order to detect the agent within the aerosol.

BRIEF DESCRIPTION OF THE SEVERAL VIEWS OF THE DRAWING(S)

Having thus described example embodiments in general terms, reference will now be made to the accompanying drawings, which are not necessarily drawn to scale, and wherein:

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. Furthermore, as used herein, the term "or" is to be interpreted as a logical operator that results in true whenever one or more of its operands are true.

Detection of agents in aerosols is important in fields ranging from environmental health monitoring to biosurveillance, and current agent detectors have many weaknesses including slow detection time, expensive reagents, and the like. Accordingly, the detector, as described herein, applies the principles of microfluidics to bioaerosol detection in order to result in increased detection times while being cost effective. The detector may operate by aerodynamically focusing aerosols directly into droplets to harness the benefits of a microreactor environment. Accordingly, the detector enables the direct collection of aerosols into a convenient droplet microfluidic platform for the detection of agents in the aerosol. Moreover, the detector, as described herein, may enable for a noninvasive method for identifying agents such as influenza, by capturing a sneeze, a breath, or a cough from a human.

FIGS. 1-6 illustrate example embodiments of the detector (and related components) for detecting an agent in aerosol. Aerosol, as used herein, is defined a colloid of solid particles or liquid droplets in air or another gas. Moreover, the aerosol may be any naturally-occurring or man-made aerosol. In some cases, the aerosol particles or liquid droplets may be microscopic and have a particle diameter ranging in size from about 1 nanometer ("nm") to about 100 micrometers ("μm"). Agents, as used herein, is defined as including any chemical, nuclear, or biological agent (such as bacteria, virus, fungi, or other microorganism) that is capable of being transmitted through the air. Agents may include Anthrax, Pneumonic Plague, Tularemia, Brucellosis, Q Fever, Psittacosis, Rocky Mountain Spotted Fever, Smallpox, Dengue, Equine Encephalitis, Hantann, Congo-Crimean Hemorrhagic Fever, Ebola, Lassa, Botulinum, Staphylococcal Enterotoxin B, *Perfringens*, Ricin, Saxitoxin, Tetrodotoxin, Aflatoxin, Influenza, *Streptococcus*, Measles, Cryptococcosis, Tuberculosis, Chickenpox, Nerve Agents, Blood Agents, or the like. It should be understood that the above list is not intended to an exhaustive list but rather a representative list of agents.

Figure 1:
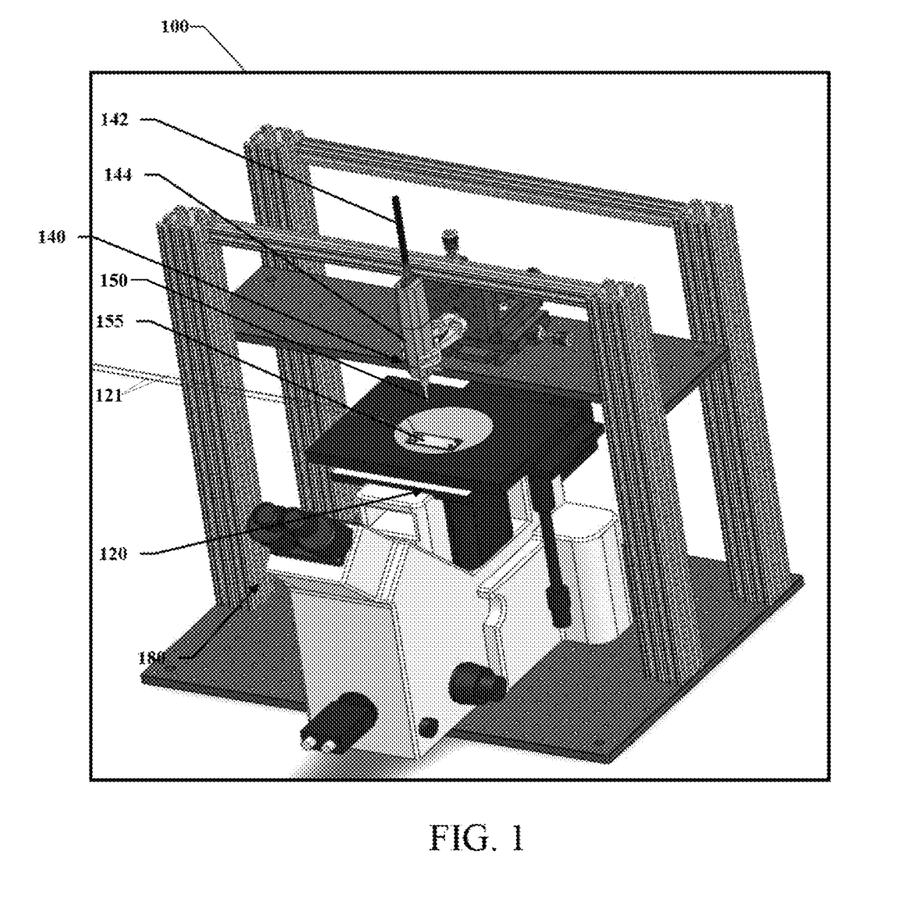
FIG. 1 illustrates a detector for detecting an agent in an aerosol according to an example embodiment.
Figure 2:
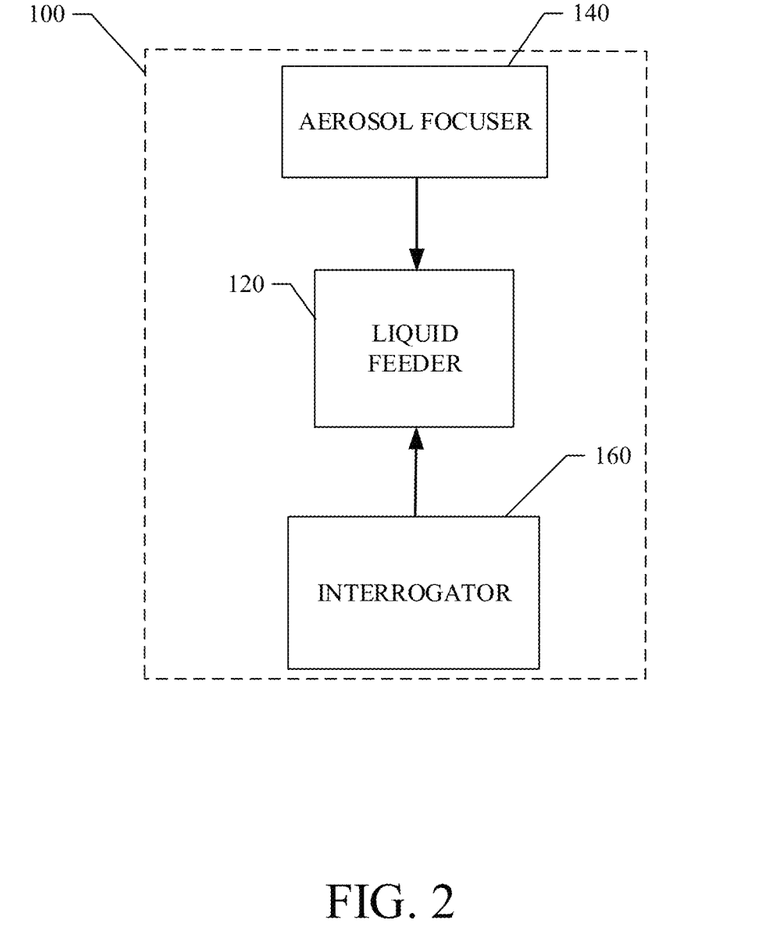
FIG. 2 illustrates a block diagram of a detector for detecting an agent in an aerosol according to an example embodiment.

As shown in FIGS. 1 and 2, the detector 100 for detecting the agent in the aerosol may include a liquid feeder 120, an aerosol focuser 140, and an interrogator 160. The liquid feeder 120 may be any device known in the art configured to receive a liquid suspension in order to form a droplet. In some cases, the liquid suspension may contain an assay reagent. The assay reagent may be any known reagent typically used in an assay such as a polymerase chain reaction (PCR) reagent, an antibody, a fluorescently-tagged antibody, fluorescent dye, quantum dot, or the like. The assay reagent used in the liquid suspension may be determined based on the type of agent that is sought to be detected. In other cases, a single type of assay reagent may be used to detect various types of agents (i.e., where there is no specific agent that is sought to be detected). In accordance with other example embodiments, when there is a specific agent sought to be detected, the liquid suspension may contain not only the assay reagent but a microbe. The microbe may act as a host for the type of agent that is being detected. Accordingly, the type of microbe used in the liquid suspension may be determined based on the type of agent that is sought to be detected.

In some cases, the liquid feeder 120 may be a T-junction or Y-junction microfluidic chip 155. The microfluidic chip 155 may be constructed from glass, silicon, polymers, or combinations thereof and may receive liquid from tubing 121. For example, in some example embodiments, the microfluidic chip 155 may be made from polydimethylsiloxane. In some cases, the length of the liquid feeder 120 may range in size from 20-50 mm, and the width of the liquid feeder may range in size from 20-50 mm.

Figure 3:
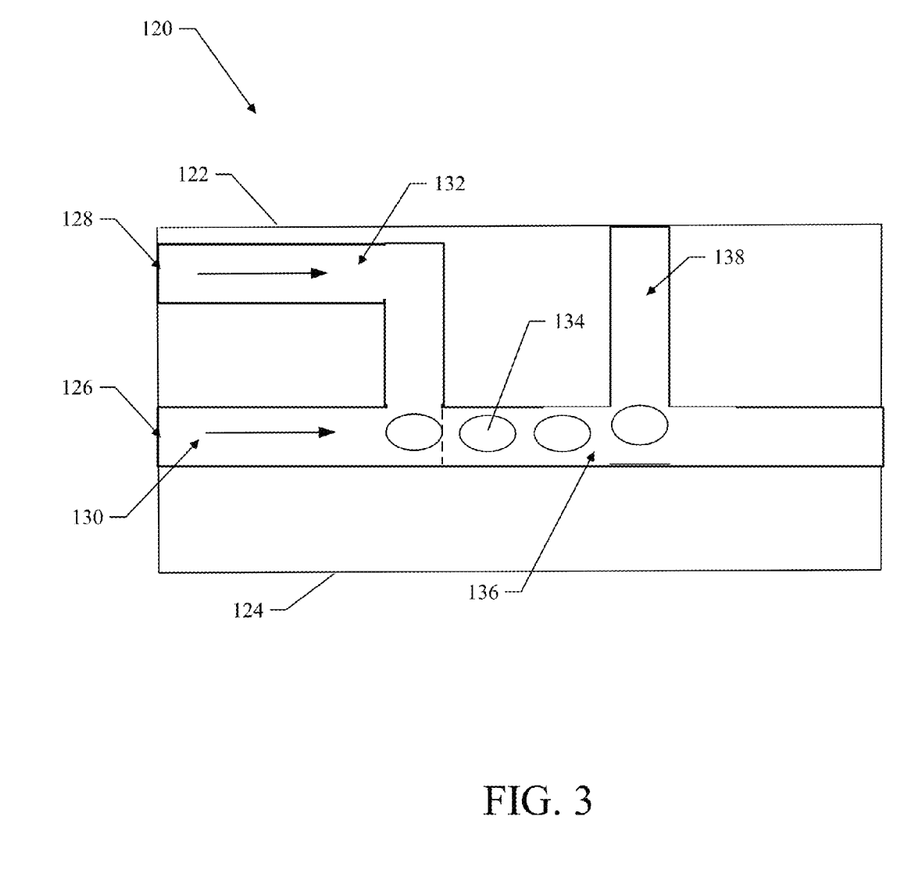
FIG. 3 illustrates a block diagram of a liquid feeder of a detector according to an example embodiment.

FIG. 3 is an example of the liquid feeder 120 according to an example embodiment contained herein. The liquid feeder 120 may have a first surface 122 and a second surface 124. A gap may exist between the first surface 122 and the second surface 124 such that a plurality of inlet ports and fluid channels are formed between the first and second surfaces 122 and 124 of the liquid feeder 120. Additionally, the first surface 122 and the second surface 124 may extend substantially parallel to each other. Moreover, the first surface 122 may be located closer to the aerosol focuser 140 of the detector 100 than the second surface 124.

As further shown in FIG. 3, the liquid feeder 120 may have an aqueous inlet port 126, an oil inlet port 128, an aqueous channel 130, and an oil channel 132 located between the first and second surfaces 122 and 124. The aqueous channel 130 may be a substantially horizontal channel that extends parallel between the first and second surfaces 122 and 124. The oil channel 132 may have at least a portion of the channel that is substantially vertical and extends perpendicular to the aqueous channel 130. It should be understood, however, that in other example embodiments the orientation of the aqueous channel 130 and the oil channel 132 could be switched. For example, the oil channel 132 could be the substantially horizontal channel that extends parallel between the first and second surfaces 122 and 124, and the liquid suspension channel 130 could have at least a portion of the channel that is substantially vertical and extends perpendicular to the oil channel 132.

A liquid suspension may be injected into the liquid feeder 120 via the aqueous port 126, and an oil may be injected into the liquid feeder 120 via the oil port 128. The oil may be added into liquid feeder 120 before the liquid suspension so that an oil layer may reside above the droplet upon creation. As discussed below, this oil may form an oil-air interface in the detection channel. Once the liquid suspension and the oil are injected into the respective aqueous and oil ports 126 and 128, the liquid suspension may flow into the aqueous channel 130, and the oil may flow into the oil channel 132.

In some cases, the aqueous and oil channels 130 and 132 may converge at a right angle T-junction. When the liquid suspension and oil converge at the T-junction, aqueous droplets 134 may be generated or produced. It should be understood that not only may oil be used to enable the generation of aqueous droplets but air or any other liquid capable of creating a droplet upon contact with the liquid suspension may be used.

The diameter of the droplet generated may vary and range from nano- to picoliter-sized aqueous droplets 134. Moreover, as the aqueous droplets 134 contain the assay reagent, the aqueous droplet 134 may serve as a microreactor (i.e., a discrete aqueous volume to enable the analysis of a single particle) to detect the presence of the agent in the aerosol.

Upon the generation of the aqueous droplets via the liquid feeder 120 of the detector 100, the droplets 134 may continue down a main channel 136 of the liquid feeder 120. As shown in FIG. 3, the main channel 136 is an extension of or otherwise operably coupled to the liquid suspension channel 130 and may continue downstream of the T-junction (the beginning of the main channel 136 is designated by the dashed line). Accordingly, the main channel 136 also extends substantially horizontal and parallel to the first and second surfaces 122 and 124. In some cases, the main channel 134 may have a depth ranging from approximately 150 µm to 200 µm and a width ranging from approximately 350 µm-400 µm. In accordance with example embodiments contained herein, a detection channel 138, which is also located downstream of the T-junction, may extend from the main channel 136 through the first surface 122 of the liquid feeder 120 creating an opening in the first surface 122 of the liquid feeder. The detection channel 138 may serve as an entry for aerosols (as discussed further below) into the droplet 134. The detection channel 138 may have a diameter of ranging from approximately from 150-200 µm.

As the droplet 134 nears the detection channel 138, a slight increase in the internal liquid pressure in the channel causes the oil residing on a top of the droplet 134 to "shed" from the emulsion and adhere to the first surface 122 of the liquid feeder 120. This allows the meta-stationary aqueous droplet 134 to protrude from the opening of the first surface 122 and present an interface for receiving the aerosol.

As further shown in FIG. 1, the detector 100 may further include the aerosol focuser 140. The aerosol focuser 140 may be configured to form an aerosol beam and to direct the aerosol beam into the aqueous droplets 134 generated via the liquid feeder 120. Therefore, the aerosol focuser 140 may be configured to enable the seeding or encapsulation of the aerosol into the droplet 134.

Figure 4:
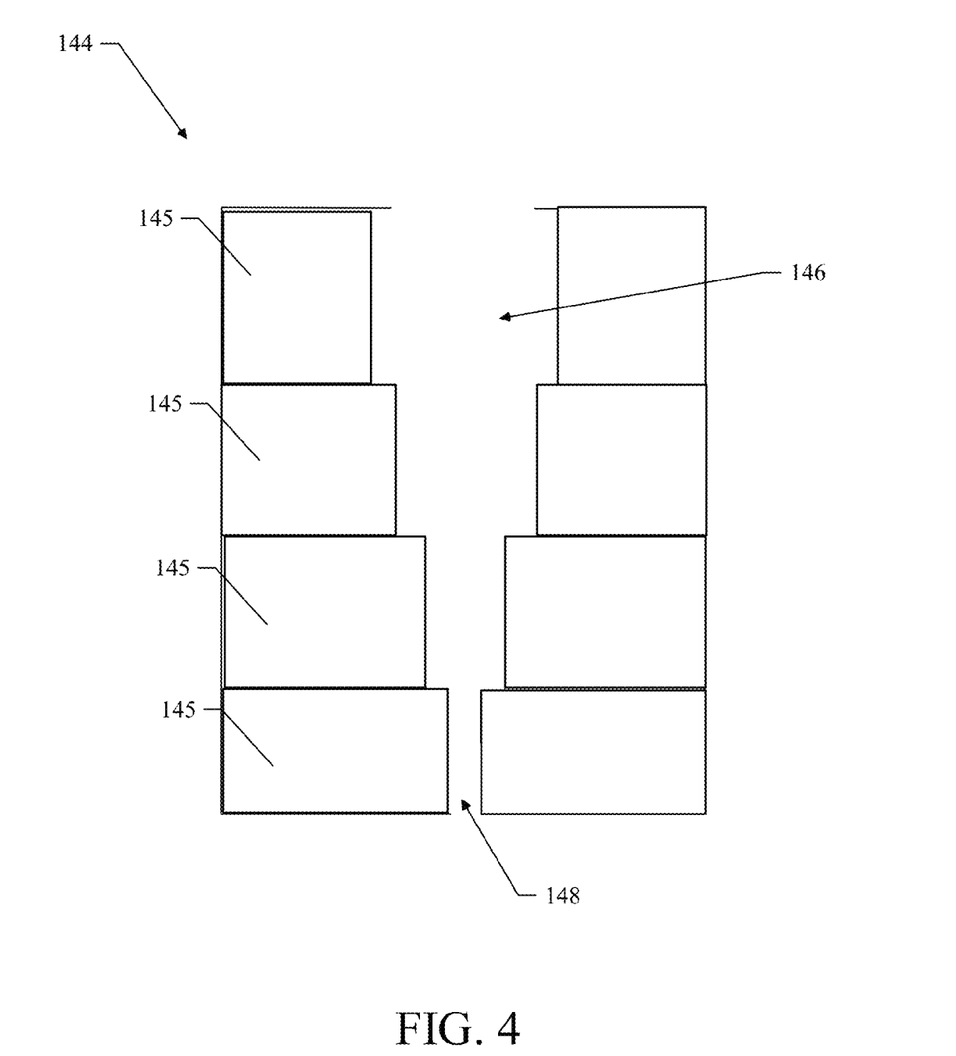
FIG. 4 illustrates a block diagram of a focuser lens of a detector according to an example embodiment.

The aerosol focuser 140 may include a focuser inlet port 142 and a focusing lens 144. As shown in FIG. 4, the aerosol may be drawn into the detector 100 via the focuser inlet port 142 into the focusing lens 144. In some cases, the detector 100 may be configured such that, when an aerosol is drawn into the focuser inlet port 142, the liquid feeder 120 simultaneously generates a droplet 134.

Moreover, the focusing lens 144 may include a plurality of slit lenses 145 arranged in a series one on top of the other. Each slit lens 145 may have a slit 146 that extends down the longitudinal centerline of the focusing lens 144 in order to form a channel that extends from the focuser inlet port 142 down to a focuser outlet port 148 of the aerosol focuser 140. The diameter of the slit 146 of each slit lens 145 may decrease progressively moving down the length of the aerosol focuser 140 toward the focuser outlet port 148 in order to successively focus and concentrate the aerosol into an aerosol beam. Accordingly, as the aerosol moves from the focuser inlet port 142 to the focuser outlet port 148, the aerosol is formed into a focused, concentrated aerosol beam to enable the aerosol to be encapsulated into the droplet 134. It should be understood that the focusing lens 144 may be referred to as an air-phase concentrator.

Figure 5:
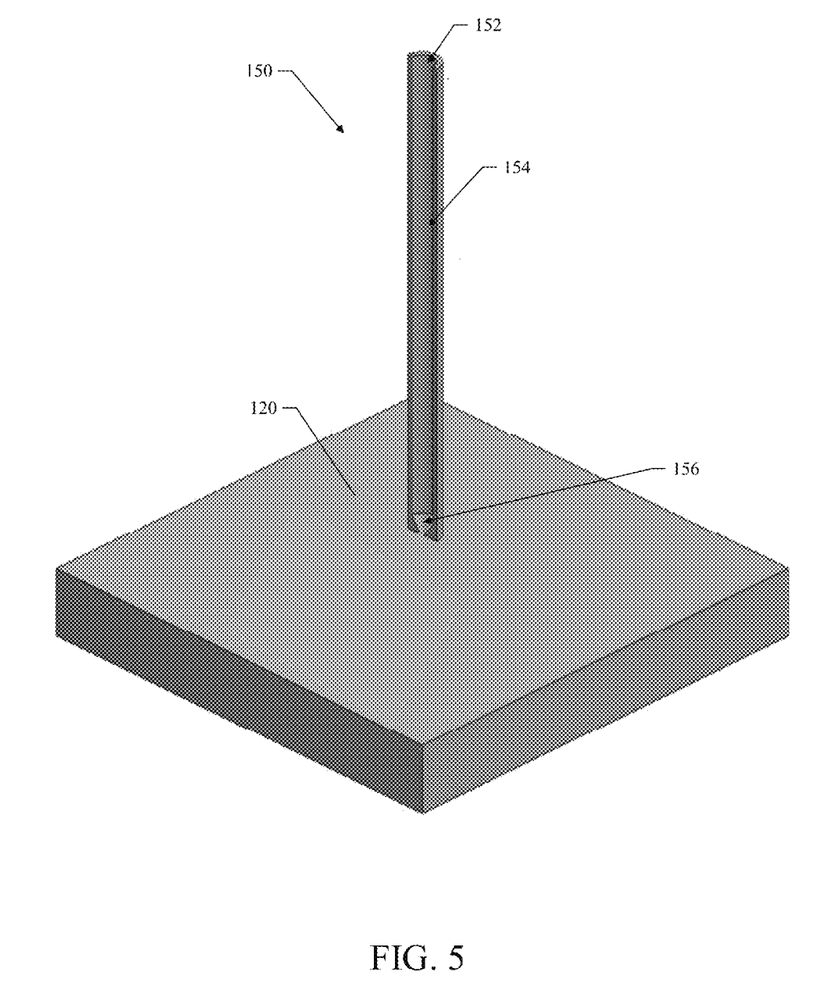
FIG. 5 illustrates a cross-section view of a capillary of a detector according to an example embodiment.

In accordance with other example embodiments contained herein, when an even more concentrated, focused aerosol beam is desired, the aerosol focuser 140 may further include a capillary 150 (see FIGS. 1 and 5). Accordingly, the aerosol beam may leave the focuser outlet port 148 and enter a capillary inlet 152 (see FIG. 5). As shown in FIG. 5, the capillary 150 may be a hollow tube 154 that has a substantially uniform diameter on the exterior surface of the capillary 150. On the interior surface of the cylinder 150, the cylinder 150 may be tapered such that the capillary 150 has a larger diameter at the capillary inlet 152 and a smaller diameter at a capillary outlet 156. Thus, the hollow cylinder 150 may have a first, larger diameter at the inlet capillary 152 that then tapers to a second, smaller diameter at the capillary outlet 156. The diameter of the capillary outlet 156 may range from 500 to 750 µm. In some cases, the capillary 150 may be tapered approximately 45°.

Figure 6:
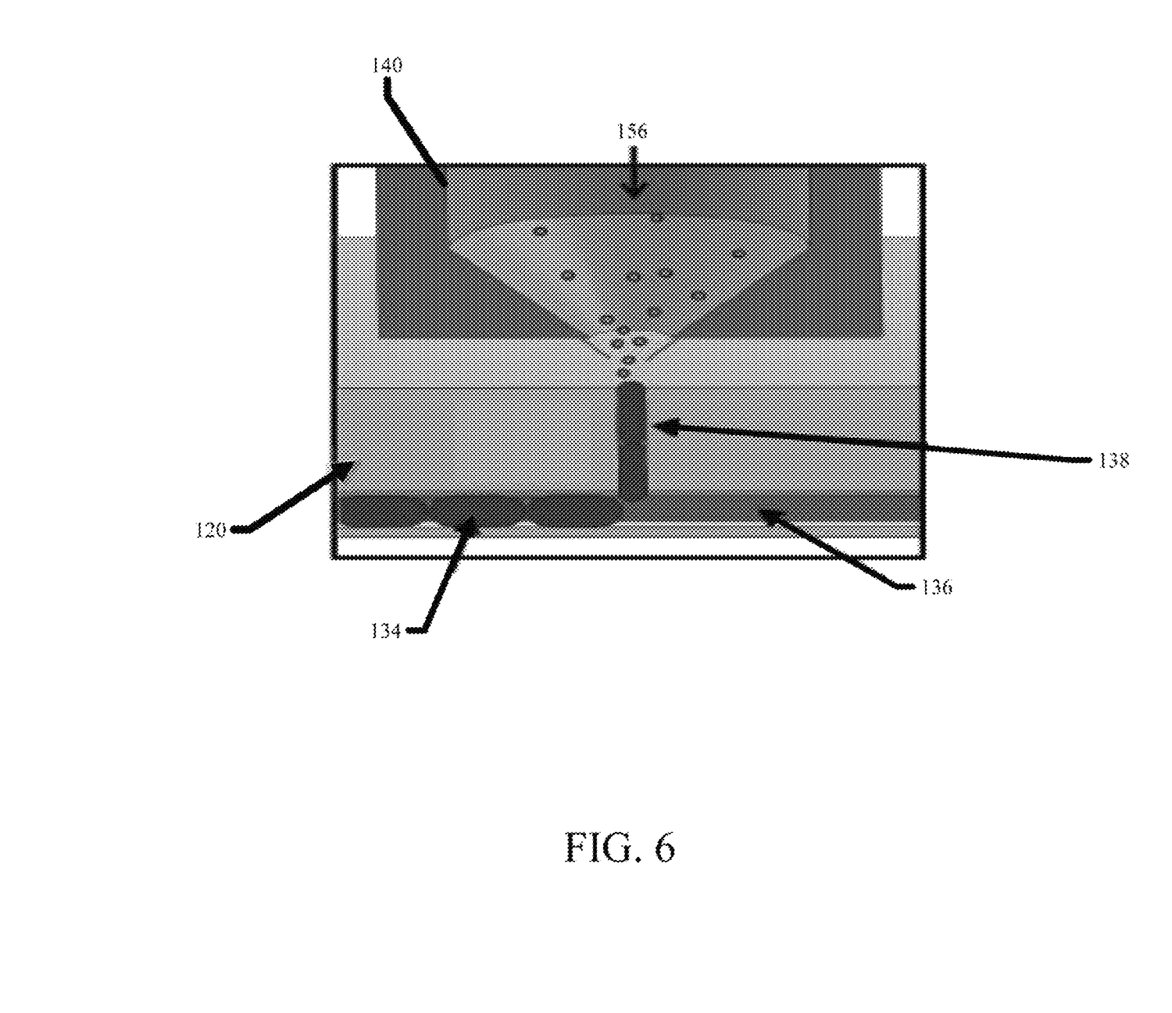
FIG. 6 illustrates a capillary of a detector according to an example embodiment.

As shown in FIG. 6, the tapering of the capillary 150 may impart a radial velocity toward a longitudinal centerline of the capillary 150 thereby effectively creating an aerosol focus point proximate the detection channel 138. It should be understood, however, that the focusing of the aerosol beam may be accomplished by other sheath-flow focusing elements known in the art.

As further shown in FIG. 6, an outlet of the aerosol focuser 140 (either the capillary outlet 156 or the focuser outlet port 146) is located above and proximate the opening of the detection channel 138. In some cases, the outlet of the aerosol focuser 140 may be located above the opening of the detection channel 138 approximately 0.2-4 mm. Additionally, as the aerosol exits the outlet of the aerosol focuser 140, the aerosol may not only be configured to focus the aerosol such that the aerosol enters the detection channel 138 but the aerosol may also be configured to penetrate into the droplet 134 upon impaction. Accordingly, the aerosol focuser 140 may be configured to accelerate the aerosol to a predetermined velocity to overcome surface tension of the droplet 134. For a non-wettable aerosol, the velocity component normal to the collection interface that is required for penetration of the droplet, may be calculated by the following Formula (I):

$$v_N = \left(\frac{8\sigma}{\rho_p d_p}\right)^{1/2} \quad \text{(I)}$$

where $\rho_p$ is the particle density, $d_p$ is the particle diameter, and $\sigma$ is the surface tension of the droplet 134.

Moreover, by positioning the aerosol focuser 140 over the opening of the detection channel 138, air pressure from the aerosol focuser 140 may "pin" or fix the droplet 134 emerging near the detection channel 138 to form an air-liquid interface at the detection channel 138 of the liquid feeder 120. This air-liquid interface formed in the detection channel 138 may serve as the target for depositing the aerosol into the droplet. Therefore, the aerosol focuser 140 may not only concentrate and focus the aerosol such that the aerosol may be encapsulated in the droplet 144 but the aerosol focuser 140 may also serve to "pin" the droplet 134 proximate the detection channel 134.

Figure 7:
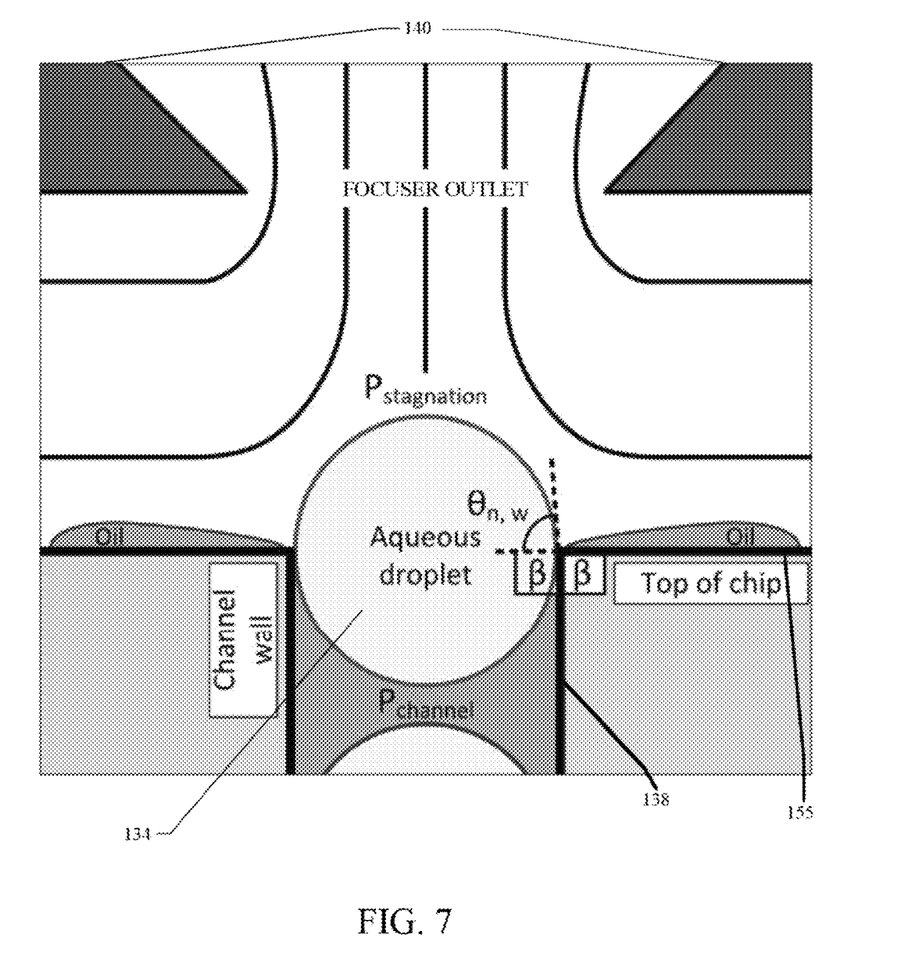
FIG. 7 illustrates a cross-section view of a liquid feeder and outlet of an aerosol focuser according to an example embodiment.

FIG. 7 illustrates the pinning of the droplet 134 via the aerosol focuser 140. The "pinning" of the droplet via the aerosol focuser 140 may occur due to a balance of forces between a stagnation air pressure from the aerosol focuser 140, interfacial forces, and internal liquid pressure in the detection channel 138. In order to "pin" the droplet proximate the detection channel, the following criterion must be satisfied: $P_{L,min} \leq P_L < P_{L,max}$, where $P_{L,min}$ and $P_{L,max}$ are the liquid pressures at the onset of the interface receding back into the detection channel and the interface bursting, respectively. $P_{L,min}$ is determined by the following Formula (II):

$$P_{L,min} = P_{stag} - \frac{4\sigma \cos \theta_e}{D} \quad \text{(II)}$$

$P_{L,max}$ is determined by the following Formula (III):

$$P_{L,max} = P_{stag} - \frac{4\sigma \cos \theta_l^*}{D} \quad \text{(III)}$$

In the above Formulas (II) and (III), $P_{stag}$ is the stagnation pressure of the outlet of the aerosol focuser, D is the diameter of the detection channel, $\sigma$ is the surface tension of the droplet, $\theta_e$ is the equilibrium contact angle, and $\theta_1$ is the contact angle associated with interface bursting.

Once the aerosol is encapsulated within the droplet, the assay reaction may react causing an assay reaction to occur. The assay reaction may determine the presence of the agent in the aerosol. Accordingly, the detector 100 may also include an interrogator 160 (see FIG. 2) that is configured to interrogate the droplet having the encapsulated aerosol to determine if any agents exist within the droplet 134. The interrogator 160 may be any device capable of causing the detection the agent. Thus, the interrogator may be a light source (such as a laser), a spectrometer, a fluorometer, a calorimeter, or the like. In some cases, when the droplet 134 is interrogated with interrogator such as a light source, the interrogator may cause a specific optical signature to appear that indicates the presence of the agent in the aerosol.

In accordance with other example embodiments herein, upon encapsulation of the aerosol into the droplet 134, the droplet 134 may be manipulated by microelectronics or electrowetting. For example, the droplet may be retracted into another channel on the liquid feeder 120 for incubation and interrogation. Moreover, the droplet may be retracted into another channel on the liquid feeder 120 for the injection of additional reagents.

In accordance with further example embodiments, the detector 100 may also include a microscope 180 (see FIG. 1) such that a user may view the results of the assay reaction. Moreover, in accordance with even further example embodiments, the detector 100 may even further include a fluorescence trigger (not shown). Agents may naturally exhibit fluorescence if probed with a light source. Accordingly, the detector 100 may include the fluorescence trigger between the focuser inlet 142 and the focuser lens 144. By including the fluorescence trigger at this location, the aerosol can be initially probed to see if the aerosol expresses fluorescence at a predetermined wavelength (i.e., giving an initial indication of an agent in the aerosol). If the aerosol does express fluorescence, the aerosol may be allowed into the focuser lens such that the aerosol can be encapsulated in the droplet. If the aerosol does not express fluorescence, the aerosol may be released from the inlet port so that the aerosol is not prepared for encapsulation into the droplet.

Figure 8A:
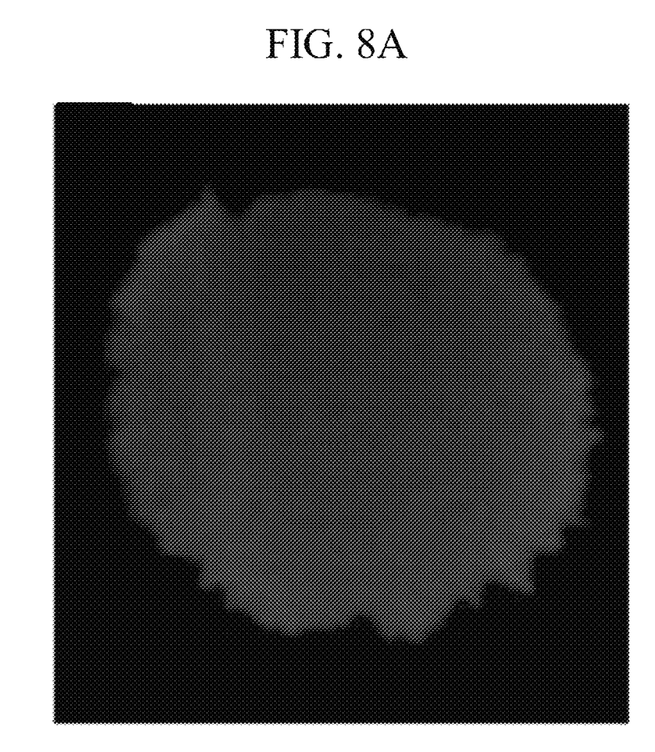
FIG. 8 illustrates a microscope imaging of an assay reaction in a droplet containing an aerosol according to an example embodiment.
Figure 8B:
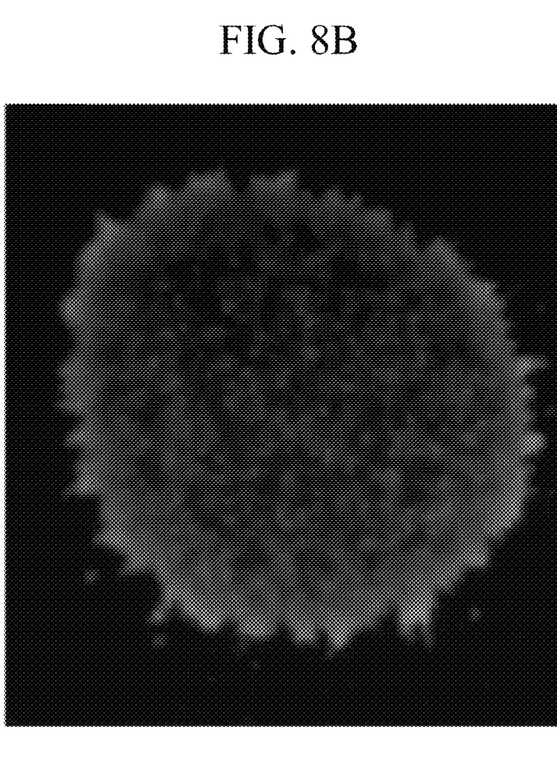

FIG. 8, which includes FIGS. 8A and 8B, are examples of an assay reaction that may occur upon the encapsulation of the aerosol into the droplet. FIG. 8A is an example of fluorescence microscope imaging of droplets containing an aerosol having no agents, after twenty seconds of incubation. FIG. 8B is an example of fluorescence microscope imaging of droplets containing a collected biological aerosol. Accordingly, after only a short period of time, the droplet may be interrogating with the interrogator 160 allowing the user to differentiate between non-biological threats and biological threats.

Figure 9:
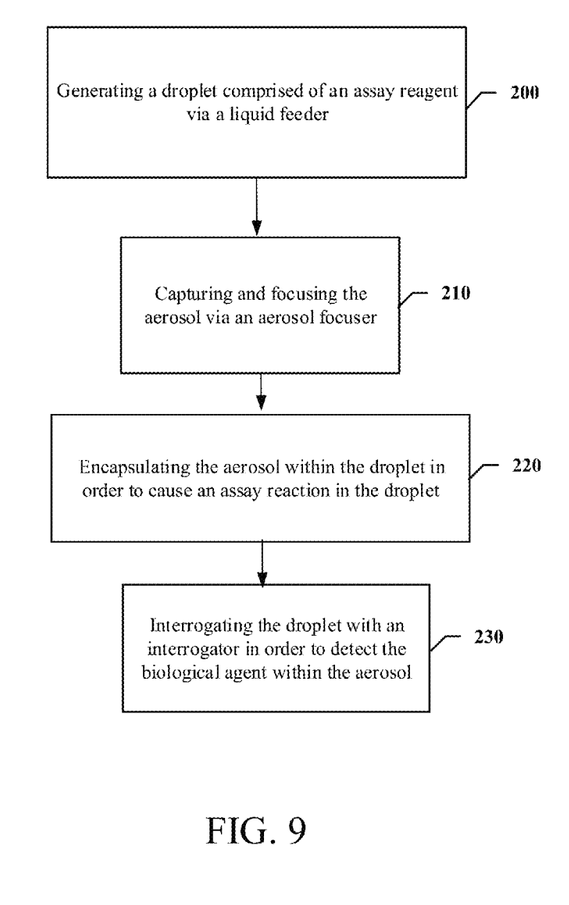
FIGS. 9-11 illustrate a method of detecting an agent in an aerosol according to an example embodiment.
Figure 10:
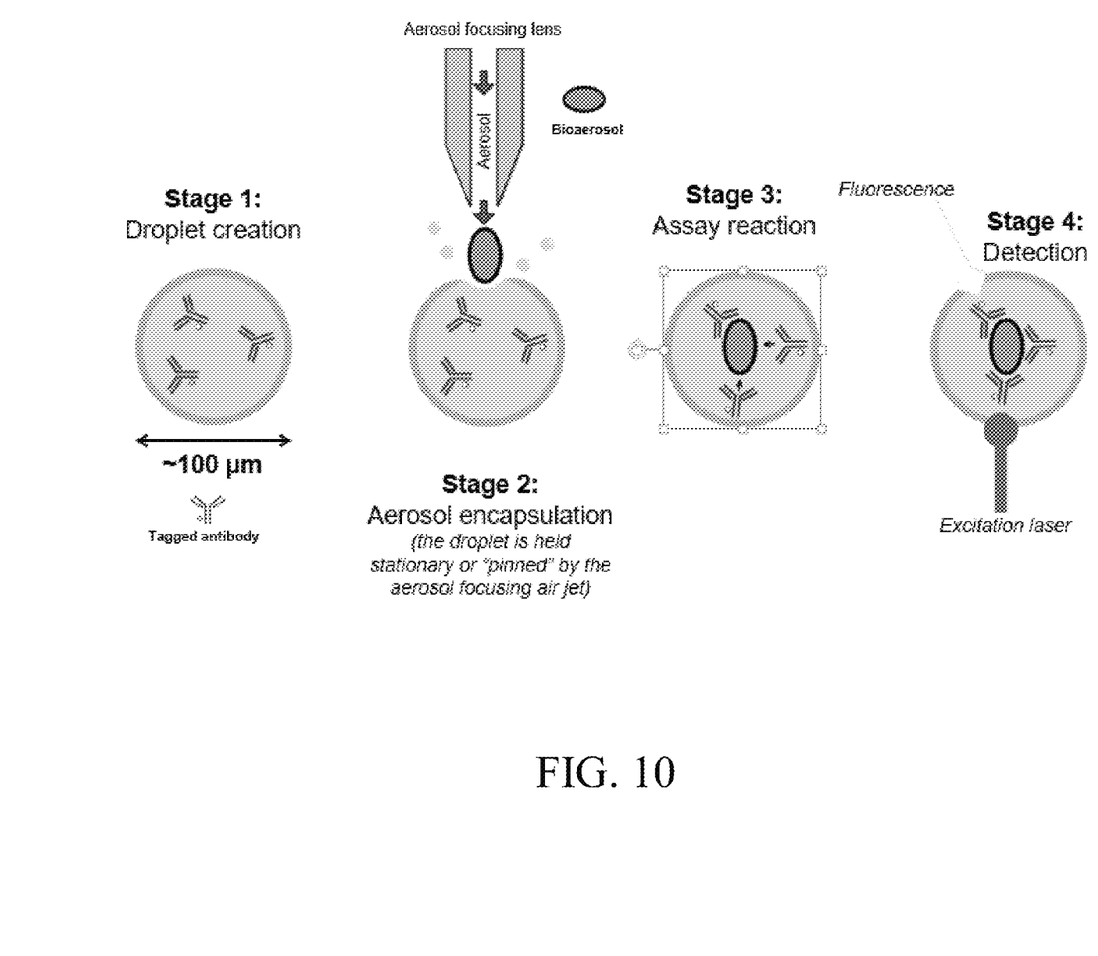
Figure 11:
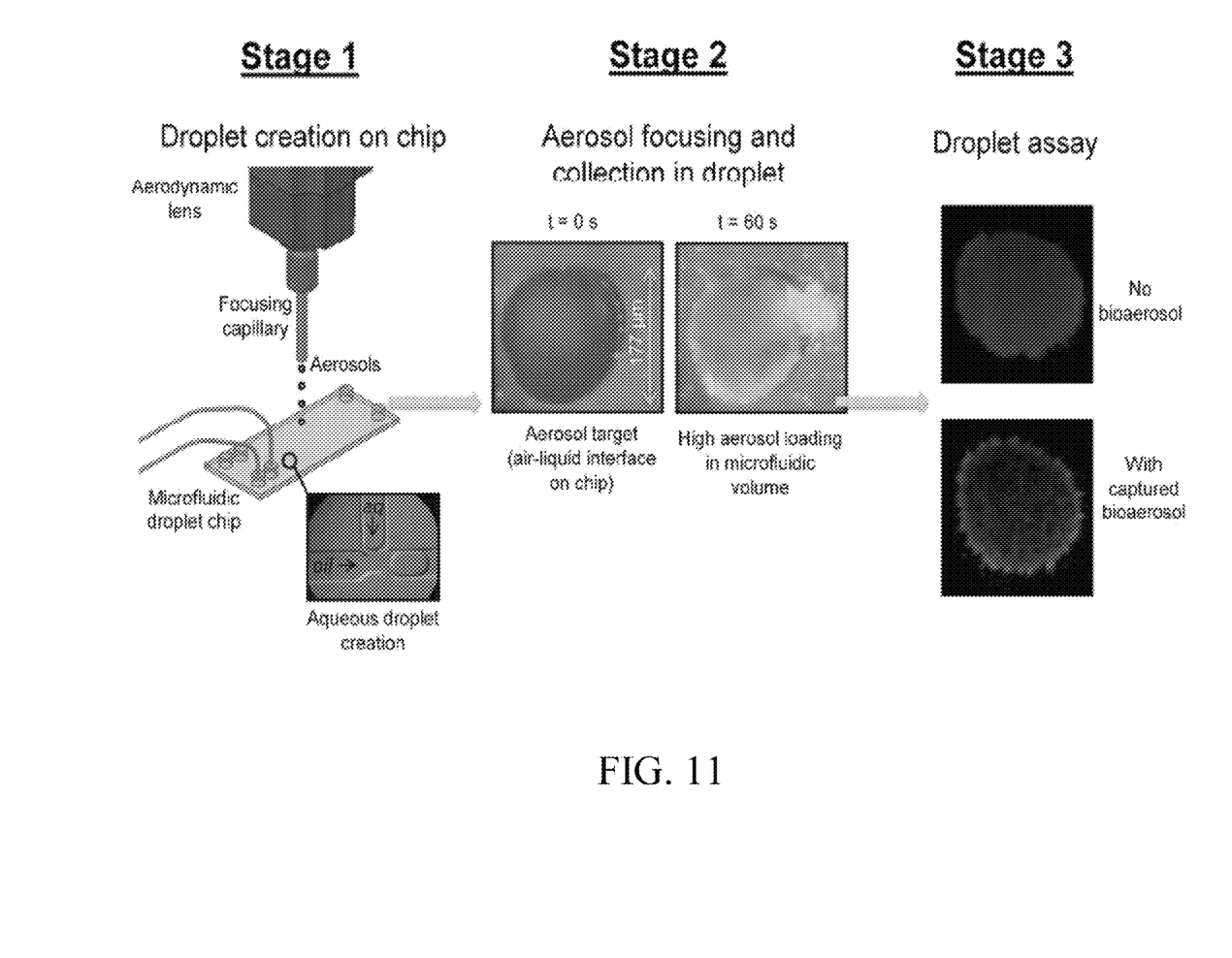

FIGS. 9-11 illustrate control flow diagrams of a method of detecting the agent via the detector. As shown in FIG. 9, the method may include generating a droplet comprised of an assay reagent via a liquid feeder, at operation 200. The method may further include capturing and focusing the aerosol via an aerosol focuser, at operation 210. At operation 220, the method may further include encapsulating the aerosol within the droplet in order to cause an assay reaction in the droplet. The method may additionally include interrogating the droplet with an interrogator in order to detect the agent within the aerosol, at operation 230.

FIGS. 10 and 11 illustrate a control flow diagram of a method of detecting the agent via the detector. Stage 1 is representative of generating the droplet comprised of an assay reagent via a liquid feeder. Stage 2 is representative of capturing and focusing the aerosol via an aerosol focuser and encapsulating the aerosol within the droplet. Stage 3 is representative of the assay reaction that occurs upon the encapsulation of the aerosol within the droplet. Stage 4 is representative of detecting the agent in the aerosol.

Example embodiments may enable the detection an agent within an aerosol. Accordingly, a detector may be provided that includes a liquid feeder configured to generate a droplet comprised of an assay reagent. The detector may further include an aerosol focuser configured to capture and focus the aerosol such that the aerosol is configured to be encapsulated within the droplet in order to cause the assay reagent to react in the droplet. The detector may even further include an interrogator configured to interrogate the droplet in order to detect the agent within the aerosol.

The detector may include various modifications, additions or augmentations that may optionally be applied. Thus, for example, in some cases, the aerosol focuser may be configured to pin the droplet proximate an outlet port of the aerosol focuser to enable encapsulation of the aerosol in the droplet. Alternatively or additionally, the liquid feeder may be configured to generate the droplet at a substantially same time as the aerosol focuser captures the aerosol. Alternatively or additionally, the liquid feeder may be configured to generate the droplet at a substantially same time as the aerosol focuser captures the aerosol. Alternatively or additionally, the assay reagent may include a fluorescently-tagged antibody, PCR reagent, fluorescent dye, or the like. Alternatively or additionally, the droplet may further include a microbe. Alternatively or additionally, the aerosol focuser may include an inlet port, an outlet port, and a focuser lens, where the focuser lens is configured to narrow and concentrate the aerosol as the aerosol moves from the inlet port to the outlet port. Alternatively or additionally, the liquid feeder may include a liquid suspension channel extending substantially horizontally between a first surface and a second surface of the liquid feeder; an oil channel having a portion extending substantially vertically between the first surface and the second surface of the liquid feeder, where the liquid suspension channel and the oil channel intersect at a right angle such that a liquid suspension in the liquid suspension channel and oil in the oil channel converge to generate the droplet. In some cases, the liquid feeder may further include a main channel and a detection channel, where the main channel is operably coupled to the liquid suspension channel and extends substantially horizontally between the first surface and the second surface of the liquid feeder downstream of the intersection of the liquid suspension channel and the oil channel, and where the droplet continues down the main channel towards the detection channel. In some cases, the detection channel may intersect with the main channel and extend vertically through the first surface of the liquid feeder to form an opening in the first surface of the liquid feeder. In some cases, the aerosol focuser may be configured to pin the droplet proximate the opening of the liquid feeder. Alternatively or additionally, the detector may further include a microscope such that the reaction of the assay reagent is observable by a user. Alternatively or additionally, the aerosol focuser may be located within 0.2-4 mm of a surface of the liquid feeder. Alternatively or additionally, the interrogator may include a light source configured to emit a light towards the droplet in order to detect the agent in the aerosol.

Many modifications and other embodiments will come to mind to one skilled in the art to which this disclosure pertains having the benefit of the teachings presented in the foregoing descriptions and the associated drawings. Therefore, it is to be understood that this disclosure is not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A detector for detecting an agent within an aerosol, the detector comprising:
   a liquid feeder configured to generate a droplet comprised of an assay reagent;
   an aerosol focuser configured to capture and focus the aerosol such that the aerosol is configured to be encapsulated within the droplet in order to cause the assay reagent to react in the droplet; and
   an interrogator configured to interrogate the droplet in order to detect the agent within the aerosol.

2. The detector of claim 1, wherein the aerosol focuser is configured to pin the droplet proximate an outlet port of the aerosol focuser to enable encapsulation of the aerosol in the droplet.

3. The detector of claim 1, wherein the liquid feeder is configured to generate the droplet at a substantially same time as the aerosol focuser captures the aerosol.

4. The detector of claim 1, wherein the assay reagent comprises a fluorescently-tagged antibody, PCR reagent, fluorescent dye, or the like.

5. The detector of claim 1, wherein the droplet further comprises a microbe.

6. The detector of claim 1, wherein the aerosol focuser comprises an inlet port, an outlet port, and a focuser lens, wherein the focuser lens is configured to narrow and concentrate the aerosol as the aerosol moves from the inlet port to the outlet port.

7. The detector of claim 1, wherein the liquid feeder comprises: a liquid suspension channel extending substantially horizontally between a first surface and a second surface of the liquid feeder; an oil channel having a portion extending substantially vertically between the first surface and the second surface of the liquid feeder, wherein the liquid suspension channel and the oil channel intersect at a right angle such that a liquid suspension in the liquid suspension channel and oil in the oil channel converge to generate the droplet.

8. The detector of claim 7, wherein the liquid feeder further comprises a main channel and a detection channel, wherein the main channel is operably coupled to the liquid suspension channel and extends substantially horizontally between the first surface and the second surface of the liquid feeder downstream of the intersection of the liquid suspension channel and the oil channel, wherein the droplet continues down the main channel towards the detection channel.

9. The detector of claim 8, wherein the detection channel intersects with the main channel and extends vertically through the first surface of the liquid feeder to form an opening in the first surface of the liquid feeder.

10. The detector of claim 9, wherein the aerosol focuser is configured to pin the droplet proximate the opening of the liquid feeder.

11. The detector of claim 1, wherein the detector further includes a microscope such that the reaction of the assay reagent is observable by a user.

12. The detector of claim 1, wherein the aerosol focuser is located within 0.2-4 mm of a surface of the liquid feeder.

13. The detector of claim 1, wherein the interrogator comprises a light source configured to emit a light towards the droplet in order to detect the agent in the aerosol.

14. A method for detecting an agent within an aerosol, the method comprising:
generating a droplet comprised of an assay reagent via a liquid feeder;
capturing and focusing the aerosol via an aerosol focuser;
encapsulating the aerosol within the droplet in order to cause the assay reagent to react in the droplet; and
interrogating the droplet with an interrogator in order to detect the agent within the aerosol.

15. The method of claim 14, wherein the method further comprises: after generating the droplet, pinning the droplet near a surface of the liquid feeder proximate an outlet of the aerosol focuser.

16. The method of claim 15, wherein the surface is within 0.2-4 mm of the outlet of the aerosol focuser.

17. The method of claim 14, wherein the generation of the droplet and the capturing and focusing of the aerosol occurring at a substantially same time.

18. The method of claim 14, wherein the assay reagent comprises one of a fluorescently-tagged antibody, a PCR reagent, a fluorescent dye, or the like.

19. The method of claim 14, wherein the droplet further comprises a microbe.

20. The method of claim 14, wherein the focusing of the aerosol comprises successively concentrating the aerosol as the aerosol moves from an inlet port to an outlet port of the aerosol focuser.

* * * * *